United States Patent
Clapp et al.

(10) Patent No.: US 6,377,223 B1
(45) Date of Patent: Apr. 23, 2002

(54) PORTABLE PATIENT MONITOR WITH ANTENNA INTEGRATED INTO HANDLE

(75) Inventors: Alan E. Clapp, Milwaukee; Eric R. Slotty, Waukesha; Michael P. Cornelson, Glendale; Scott W. Hoelscher, Milwaukee; John P. Tennessen, Richfield, all of WI (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 0 days.

(21) Appl. No.: 09/438,170

(22) Filed: Nov. 11, 1999

(51) Int. Cl.[7] .................................................. H01Q 1/24
(52) U.S. Cl. ...................................... 343/718; 343/702
(58) Field of Search ................................ 343/718, 702; 455/90

(56) References Cited

U.S. PATENT DOCUMENTS 4,689,611 A * 8/1987 Franklin ...................... 340/539
6,188,362 B1 * 2/2001 Igarashi ...................... 343/702

* cited by examiner

Primary Examiner—Don Wong
Assistant Examiner—James Clinger
(74) Attorney, Agent, or Firm—Ostrager Chong & Flaherty LLP

(57) ABSTRACT

An antenna is integrated into the handle of a portable patient monitor or other portable medical diagnostic instrument to enable wireless communication with a central station. The handle is made of a rugged plastic material, e.g., polycarbonate, which protects the antennae against damage. In addition, the plastic material used in the handle does not negatively impact RF transmissions to and from the antenna. The antenna is supported in a pair of slots formed in respective ribs of a molded piece forming a part of the handle.

19 Claims, 5 Drawing Sheets

PORTABLE PATIENT MONITOR WITH ANTENNA INTEGRATED INTO HANDLE

FIELD OF THE INVENTION

This invention generally relates to portable medical diagnostic equipment. In particular, the invention relates to equipment used to monitor patients at a remote location or during transport in a hospital or other patient care setting.

BACKGROUND OF THE INVENTION

When providing medical care to patients, it is frequently necessary to monitor the patient using medical monitoring instruments. One type of instrument, the patient monitor, is capable of monitoring the patient to acquire electrocardiogram data, cardiac output data, respiration data, pulse oximetry data, blood pressure data, temperature data and other parameter data. In particular, lightweight portable monitors exist which can be moved with the patient, allowing continuous monitoring during patient transport. Also these portable monitors can be used at locations remote from a central station in a hospital facility or other patient care setting.

To facilitate monitoring at remote locations or during patient transport, modern portable patient monitors are powered by rechargeable batteries. Extended-use batteries, with quick recharge times, help maximize monitor availability. Advanced monitors have a smart battery management system which maximizes battery life, reducing maintenance and replacement. These patient monitors can also be plugged into any conventional electrical power system for use, e.g., at the patient's bedside, before and/or after the patient is transported. At the bedside, advanced patient monitors can be hardwired to a central station via a local area network (LAN) for enhanced patient surveillance efficiency. In addition, the most advanced patient monitors have a built-in wireless option which enables the monitor to go mobile without sacrificing connectivity. Such monitors also support importation of demographic and laboratory data from a hospital information system for increased efficiency.

Portable patient monitors with integral battery power supply are commercially available in a compact, ergonomic package which allows easy handling. Typically such monitors have a drop-tested rugged design which allows them to withstand the punishment of the demanding intra-hospital transport applications. Mounting options make these monitors ideally suited for headboard/footboard, siderail, rollstand and IV pole use. The compact design is achieved in part through the use of flat display panels. The color or monochrome screen accommodates all numerics and multiple waveforms.

In addition to displaying waveforms and numerics representing the data being acquired, advanced patient monitors have a central processing system which stores and analyzes the acquired data. In particular, the central processing system is programmed with algorithms for analyzing the acquired data. The central processing system controls the transfer of data to the display panel for display and to the LAN via either a hardwired or wireless connection.

Known patient monitors incorporate an optional radiofrequency local area network (RF LAN) feature that utilizes antenna diversity technology. Antenna diversity technology uses the stronger signal from two antennae to reduce multipath RF interference and provide redundancy. To maximize transmissions, the antennae should be mounted a minimum distance of one-quarter wavelength apart on the top surface of the monitor. An antenna mounted on a portable device is exposed to the risk of damage during monitor movement. Damage to the antenna could result in a non-functional RF LAN subsystem in the monitor. Thus, there is a need for a portable wireless instrument in which the antennae are not inherently susceptible to damage.

SUMMARY OF THE INVENTION

The present invention mitigates potential damage to an antenna of a portable wireless instrument, such as a patient monitor, by incorporating the antenna inside the instrument handle. The handle is made of material which does not negatively impact RF transmissions and which is sufficiently rugged to protect the antennae against damage when the instrument is subjected to impacts. The preferred material is a plastic such as polycarbonate.

In accordance with the preferred embodiment of the invention, a pair of antennae are integrated into the handle of a portable patient monitor to enable wireless communication with a central station. The handle comprises front and rear molded pieces which are fastened together, the antennae being mounted to one of the molded pieces. Each antenna is securely supported in a respective pair of slots formed in respective ribs of the molded piece. In the assembled state, the front and rear molded pieces of the handle protect the antennae against impacts.

The invention is not limited in application to handles designed to house two or more antennae. The construction technique disclosed herein can be employed in portable instruments having a single antenna.

DETAILED DESCRIPTION OF THE PREFERRED EMBODIMENTS

Figure 1:
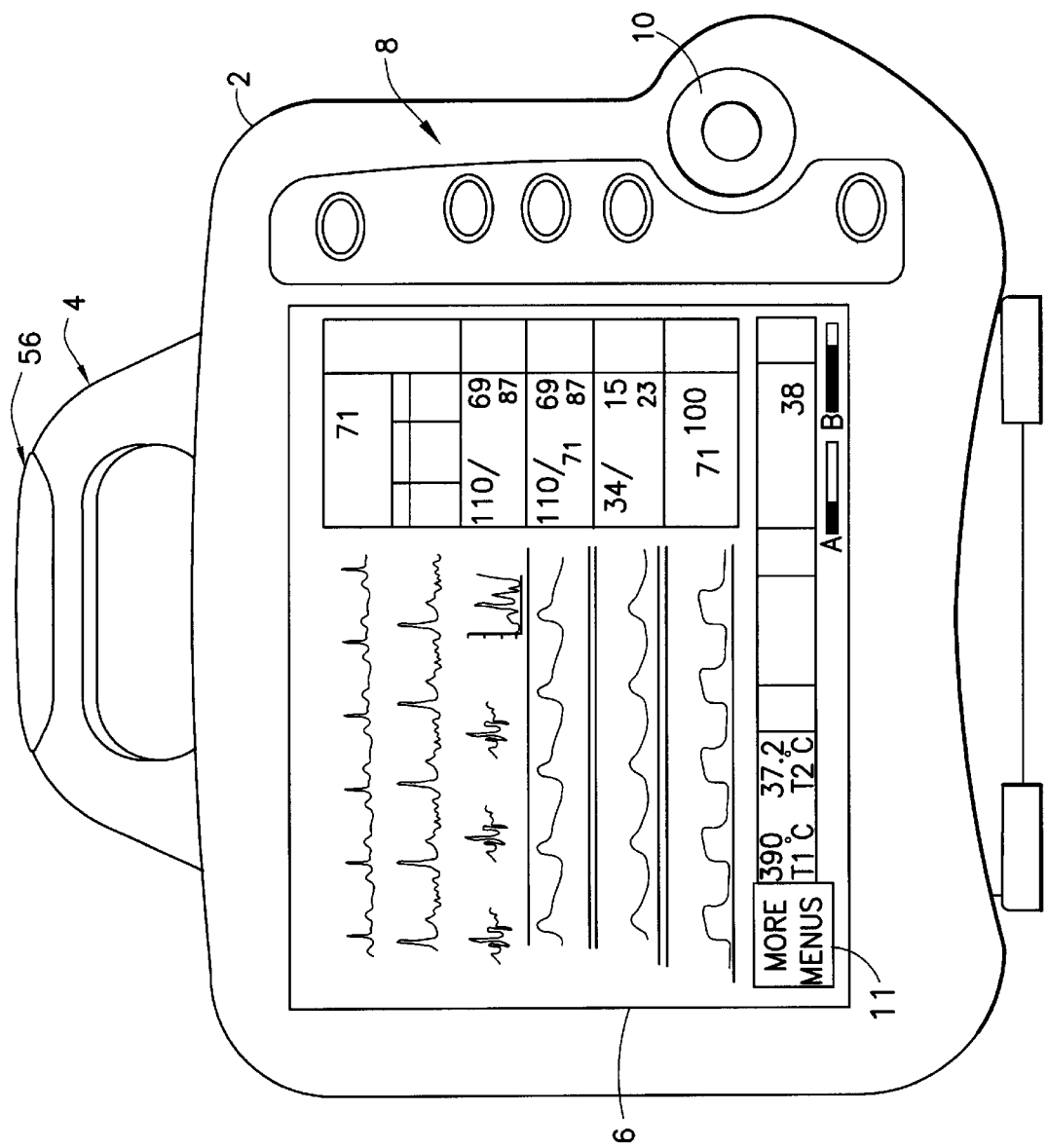
FIG. 1 is a drawing showing a generally frontal view of a portable patient monitor in accordance with the preferred embodiment of the invention.

A portable patient monitor, depicted in FIG. 1, comprises a housing 2 and a handle 4 connected to the top of the housing. Reference numeral 56 identifies a lens of an alarm light assembly, which will be described in more detail later. The monitor further comprises a flat display panel 6 secured in a generally rectangular window formed in the front face of the housing 2. An operator interface comprises a plurality of keys, forming a keypad 8, and a so-called "trim" knob 10, which allows the user to select and focus on a particular menu. The display panel 6 displays waveforms and numerical data. The status of a pair of batteries A and B is indicated in the lower right-hand corner of the display panel. A "soft" operator-actuated menu key 11, appearing in the lower left-hand corner, can be used to call up additional menus.

Figure 2:
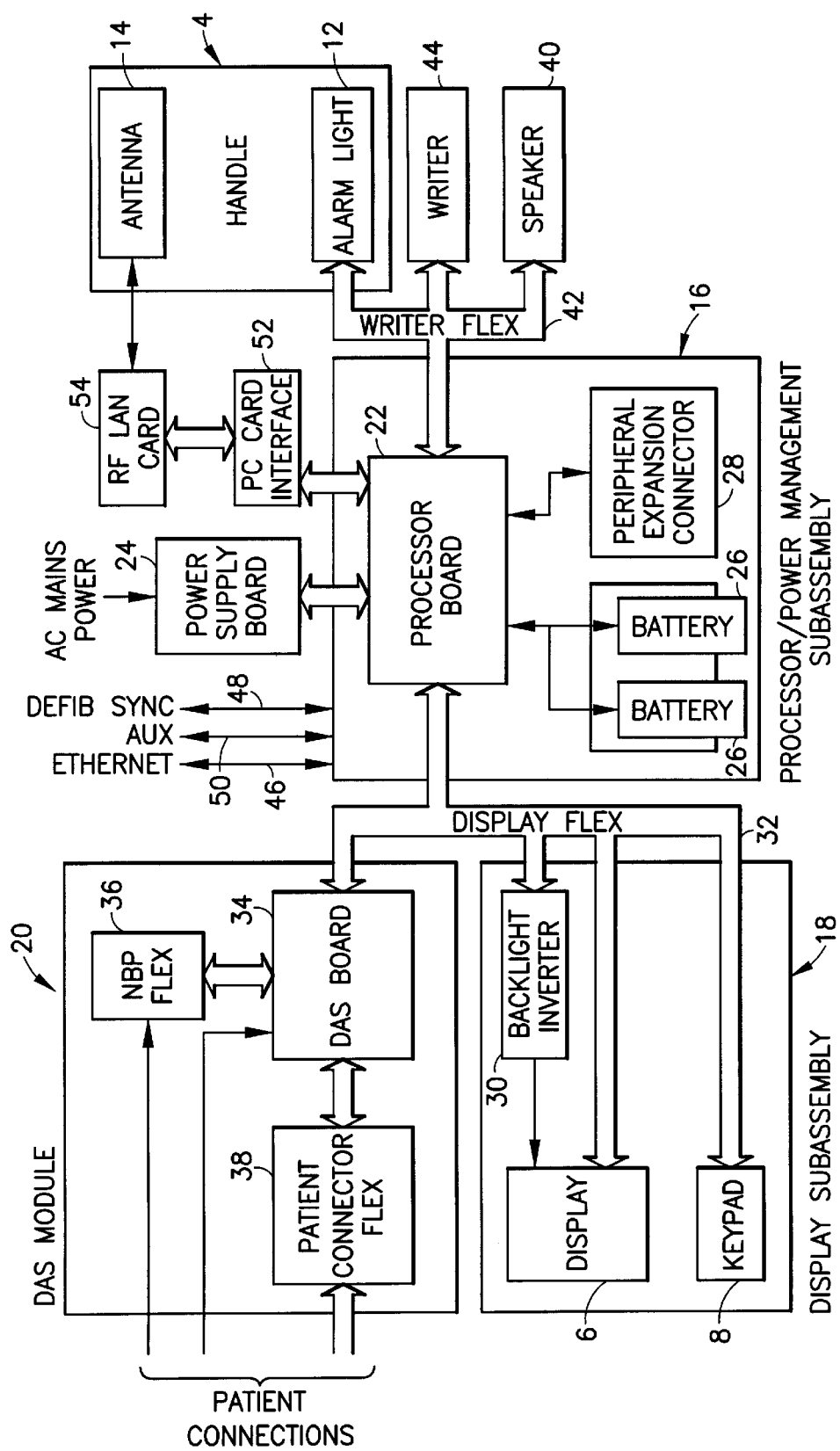
FIG. 2 is a block diagram showing a patient monitor with an antenna integrated into the handle in accordance with the preferred embodiment of the invention.

In accordance with the preferred embodiment of the invention, a pair of antennae 14 are integrated into the monitor handle 4, as generally represented in the block diagram of FIG. 2. For the sake of completeness, FIG. 2 also shows the basic internal structure of the portable patient monitor depicted in FIG. 1. Although FIG. 2 (as well as FIGS. 3, 7 and 8) also shows an alarm light 12 integrated into the handle, this is the subject of a copending patent application.

The preferred embodiment shown in FIG. 2 comprises a processor/power management subassembly 16, a display subassembly 18 and a data acquisition system module 20, each of which will be described below.

The processor/power management subassembly 16 comprises a processor board 22 powered by an ac mains power supply via a power supply board 24. Alternatively, the processor board 22 can be powered by rechargeable batteries 26 when the patient monitor is disconnected from the mains power supply, e.g., during patient transport. The processor/power management subassembly 16 further comprises a peripheral expansion connector 28, which allows the processor to communicate with peripheral processors added as the result of future expansion of the system.

The display subassembly 18 comprises a liquid-crystal display (LCD) flat panel 6, a backlight inverter 30 for powering the fluorescent tubes of the flat display panel and a keypad 8 for operator inputs. The flat display panel 6, the backlight inverter 30 and the keypad 8 are electrically coupled to the processor board 22 via a display flexible printed circuit board (flex) 32.

The data acquisition system (DAS) module 20 comprises a plurality of ports for patient connections and a DAS board 34. The patient connection for acquiring noninvasive blood pressure (NBP) data is coupled to the DAS board 34 via an NBP flex 36. The leads for acquiring electrocardiogram (ECG), respiratory and other cardiovascular data are coupled to the DAS board 34 via a patient connector flex 38. The ECG leads connect to electrodes attached to the patient's chest. The acquired data is sent to the processor board 22 for signal processing and analysis via the display flex 32. The processor board 22 controls the display panel 6 to display the desired waveforms and numerical data based on the acquired data received from the DAS board 34.

In addition to displaying acquired data, the patient monitor depicted in FIG. 2 also has the capability of automatically activating audible and visual alarms in response to acquired data exceeding a preset alarm threshold. The alarm thresholds are user-selectable via keypad entries. The visual alarm indicator is an alarm light 12 built into the monitor handle 4 which flashes when activated; the audible indicator is an audio speaker 40 which emits alarm tones when activated. The alarm light 14 and audio speaker 40 are controlled by the processor board 22 via a writer flex 42. The processor board also controls a writing device 44, e.g., a thermal recorder, via the writer flex 42. The writer 44 serves to create a written record of selected data readings.

The patient monitor shown in FIG. 2 also has the ability to communicate with a LAN (not shown) via a hardwired Ethernet connection 46, with a defibrillator (not shown) via connection 48 and with an auxiliary piece of equipment (not shown), e.g., a ventilator or a remote control device, via connection 50. The processor board provides synchronization signals to the defibrillator via connection 48. Also the patient monitor can communicate wirelessly with the LAN using a pair of antennae 14, which are also preferably integrated into the monitor handle 4. The processor board 22 sends signals to and receives signals from the antennae 14 via a PC card interface 52 which interfaces with a RF LAN card 54. The PC card interface 52 plugs into a socket which resides on the processor board 22. The RF LAN card comprises digital-to-analog converters for converting digital signals from the processor into RF signals, a transmitter for pulsing the antennae 14 to transmit the RF signals, a receiver for receiving RF signals from the antennae 14, and analog-to-digital converters for converting received RF signals into digital signals in a format acceptable to the processor. The RF LAN feature utilizes antenna diversity technology. The antenna diversity technique uses the stronger of the two signals respectively received via the antennae 14 to reduce multipath RF interference and provide redundancy.

Figure 3:
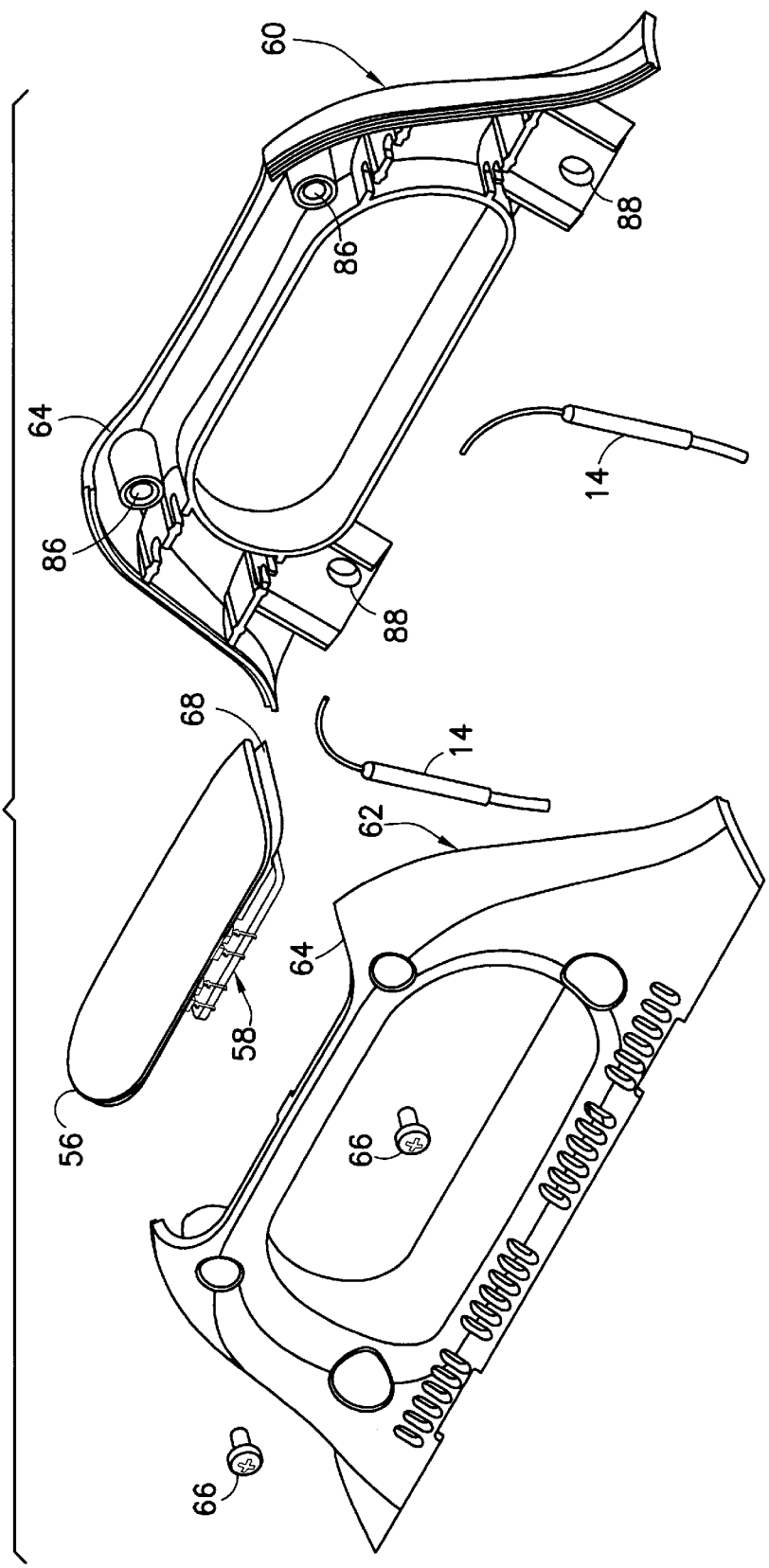
FIG. 3 is a drawing showing an exploded view of the monitor handle with integrated antennae in accordance with one preferred embodiment of the invention.

A handle incorporating antennae in accordance with the preferred embodiment is shown in FIG. 3. The handle 4 comprises two molded pieces made of opaque plastic material: a front handle part 60 and a rear handle part 62. Both parts are designed with cutouts 64 which, when the two parts of the handle are fastened together by screws 66, form an opening in which an alarm light assembly, comprising a lens 56 and a printed circuit board 58, is securely installed. Through holes 86 are molded in the front handle part 60 and threaded holes (not visible in FIG. 3) are molded in the rear handle part 62 for receiving the screws 66. The handle 4 is preferably mounted at an inclined angle relative to the monitor housing, as seen in FIG. 1. In the preferred embodiment, the assembled handle is attached to the monitor housing by screws (not shown in FIG. 3). For this purpose, one pair of throughholes 88 are provided in the front handle part 60. Another pair of throughholes (not visible in FIG. 3) are provided in the rear handle part 62. The screws for attaching the handle have threaded ends which threadably engage threaded holes (not shown) in the monitor housing.

Figure 4:
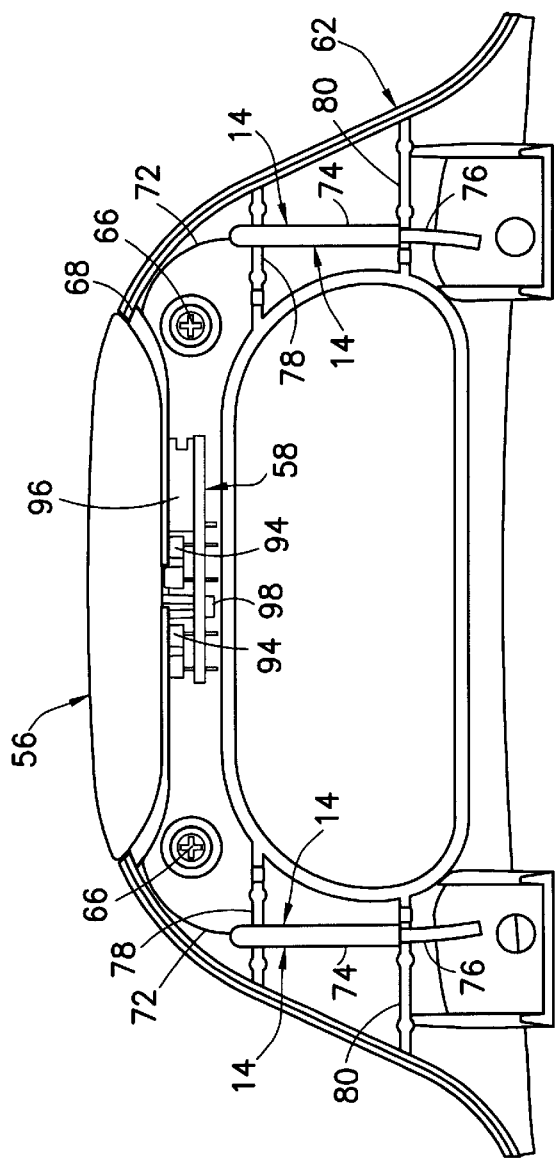
FIG. 4 is a drawing showing an elevational rear view of the assembled handle in accordance with the preferred embodiment, with the rear handle piece being removed.
Figure 6:
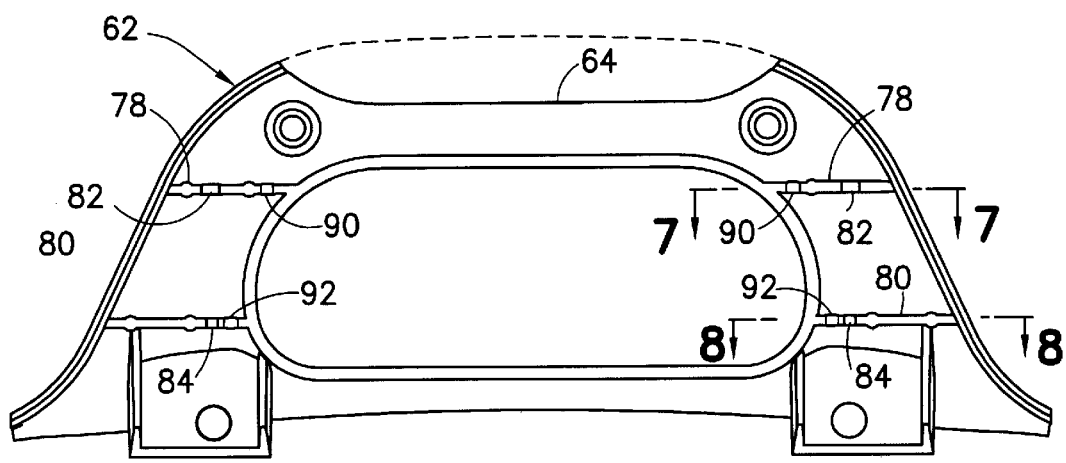
FIG. 6 is a drawing showing an elevational rear view of the front piece of the handle shown in FIG. 3.

Referring to FIG. 4, the preferred embodiment of the invention comprises a pair of antennae 14. Each antenna 14 comprises a thin metal core 72, a brass outer tube 74 and a coaxial cable 76. In conventional fashion, the thin metal core 72 is connected to a central conductor of the coaxial cable 76, while the brass outer tube 74 is connected to an outer tube in the coaxial cable 76. The exposed core 72 may optionally be coated with an insulating material.

FIG. 4 shows the handle with the rear handle piece removed. The front handle piece comprises two sets of stiffening ribs 78 and 80 molded into the concave legs of the front handle piece. Each set of ribs 78 and 80 supports one antenna 14. Preferably the ribs are generally mutually parallel. Rib 78 supports a portion of the brass metal tube 74, while rib 80 supports a portion of the coaxial cable 76. Although not shown, the rear handle piece is also provided with two sets of stiffening ribs molded into its concave legs.

Figure 7:
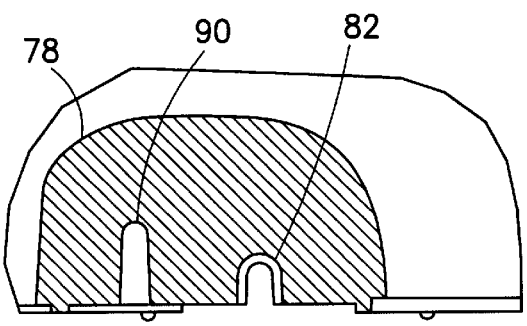
FIGS. 7 and 8 are drawings showing sectional views of two ribs forming part of the front handle piece, the sections being respectively taken along lines 7—7 and 8—8 indicated in FIG. 6.
Figure 8:
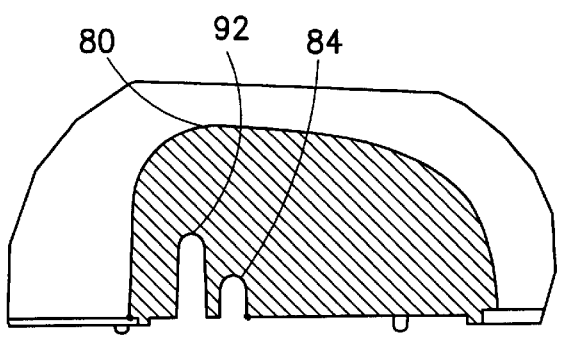

As best seen in FIG. 7, each rib 78 has a pair of slots 82 and 90. As best seen in FIG. 8, each rib 80 has a pair of slots 84 and 92. The centerlines of slots 82 and 84 are generally coplanar, the plane of the centerlines in turn being generally perpendicular to the generally mutually parallel ribs. This alignment of the slots 82 and 84 is best seen in FIG. 7, which shows a rear view of the front handle piece 60 with the antennae removed. The alarm light cable (not shown) is installed in slots 90 and 92. Each slot has a semicircular termination and a draft (i.e., degree of taper) of a few degrees (e.g., 2°) to facilitate removal of the molded front handle piece from the mold. The diameter of the semicircular end of slot 82 in rib 78 is greater than the diameter of the semi-circular end of slot 84 in rib 80 to accommodate the diameter of the brass metal tube, which is larger than the diameter of the coaxial cable. The antennae are held in place by a small amount of adhesive during assembly.

Figure 5:
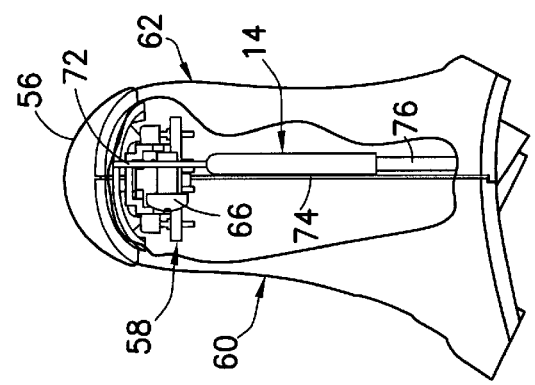
FIG. 5 is a drawing showing an elevational end view of the assembled handle in accordance with the preferred embodiment, with the front and rear handle pieces being outlined in dashed lines.

Referring to FIGS. 4 and 5, the alarm light is an assembly comprising a curved lens 56 made of molded plastic material and a printed circuit board 58 attached to a stake 98 integrally connected to the underside of lens 56. The printed circuit board 58 carries four light-emitting diodes (LEDs) 94 in a 2×2 layout, two red LEDs and two yellow LEDs. The LEDs 94 are connected to the processor board (22 in FIG. 3) by means of a connector 96, which is also mounted on the printed circuit board 58, and an alarm light cable, not shown. A groove 68 is formed along the periphery of lens 56. When the handle is assembled, the edges of cutouts 64 (best seen in FIG. 3) engage the peripheral groove 68, thereby securely holding the alarm light assembly in place. The LEDs are activated when the processor determines from the acquired data that an alarm state exists.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. In particular, the person skilled in the art will readily appreciate that the number of antennae need not be two. For example, a single antenna can be used in portable instruments which do not use antenna diversity technology. Any number of antennae incorporated within the handle of a portable instrument is within the scope of the invention. Therefore it is intended that the invention not be limited to the particular embodiment disclosed as the best mode contemplated for carrying out this invention, but that the invention will include all embodiments falling within the scope of the appended claims.

What is claimed is:

1. A portable instrument comprising:
   a stiff handle made of electrically insulating material and having an interior volume;
   an antenna housed inside said interior volume of said handle;
   a housing, said handle being rigidly attached to said housing;
   an RF transmitting system located within said housing and coupled to said antenna;
   a data acquisition system located within said housing; and
   a processor located within said housing and coupled to receive acquired data from said data acquisition system and send acquired data to said RF transmitting system.

2. The portable instrument as recited in claim 1, wherein said handle comprises a first member which supports a first portion of said antenna and a second member which supports a second portion of said antenna.

3. The portable instrument as recited in claim 2, wherein said first portion of said antenna comprises a metal outer tube and said second portion of said antenna comprises a coaxial cable.

4. The portable instrument as recited in claim 1, wherein said handle comprises a first rib having a first slot formed therein, a first portion of said antenna being disposed in said first slot.

5. The portable instrument as recited in claim 4, wherein said handle comprises a second rib having a second slot formed therein, a second portion of said antenna being disposed in said second slot.

6. The portable instrument as recited in claim 5, wherein said handle comprises first and second molded pieces, said first and second ribs being parts of said first molded piece.

7. The portable instrument as recited in claim 5, further comprising means for securing said antenna in said first and second slot.

8. The portable instrument as recited in claim 4, wherein said first slot has first and second sidewalls connected by a rounded termination, said first and second sidewalls having a degree of taper.

9. A handle comprising:
   first and second molded pieces made of electrically insulating material and defining an interior volume, wherein said first molded piece comprises a first rib traversing said interior volume and having a first slot formed therein;
   an antenna disposed inside said interior volume and supported by said first molded piece, a first portion of said antenna being disposed in said first slot;
   means for securing said first portion of said antenna in said first slot; and
   means for fastening said first and second molded pieces together.

10. The handle as recited in claim 9, wherein said handle comprises a second rib having a second slot formed therein, a second portion of said antenna being disposed in said second slot.

11. The handle as recited in claim 10, wherein said first portion of said antenna comprises a metal outer tube and said second portion of said antenna comprises a coaxial cable.

12. The handle as recited in claim 9, wherein said first slot has first and second sidewalls connected by a rounded termination, said first and second sidewalls having a degree of taper.

13. A portable patient monitor comprising:
   a housing;
   a stiff handle rigidly attached to said housing and made of electrically insulating material;
   an antenna housed inside said handle;
   an RF transmitting system located within said housing and coupled to said antenna;
   a data acquisition system located within said housing; and
   a processor located within said housing and coupled to receive acquired data from said data acquisition system and send acquired data to said RF transmitting system.

14. The patient monitor as recited in claim 13, wherein said handle comprises a first member which supports a first portion of said antenna and a second member which supports a second portion of said antenna.

15. The patient monitor as recited in claim 14, wherein said first portion of said antenna comprises a metal outer tube and said second portion of said antenna comprises a coaxial cable.

16. The patient monitor as recited in claim 13, wherein said handle comprises a first rib having a first slot formed therein, a first portion of said antenna being disposed in said first slot.

17. The patient monitor as recited in claim 16, wherein said handle comprises a second rib having a second slot formed therein, a second portion of said antenna being disposed in said second slot.

18. The patient monitor as recited in claim 17, wherein said handle comprises first and second molded pieces, said first and second ribs being parts of said first molded piece.

19. The patient monitor as recited in claim 16, wherein said first slot has first and second sidewalls connected by a rounded termination, said first and second sidewalls having a degree of taper.

* * * * *